United States Patent [19]

Soubeiran

[11] Patent Number: 5,720,746
[45] Date of Patent: Feb. 24, 1998

[54] DEVICE FOR DISPLACING TWO BODIES RELATIVE TO EACH OTHER

[76] Inventor: Arnaud André Soubeiran, 24, Villa de Lourcine, 75014 Paris, France

[21] Appl. No.: 849,058

[22] PCT Filed: Nov. 8, 1995

[86] PCT No.: PCT/FR95/01472

§ 371 Date: May 15, 1997

§ 102(e) Date: May 15, 1997

[87] PCT Pub. No.: WO96/15377

PCT Pub. Date: May 23, 1996

[30] Foreign Application Priority Data

Nov. 16, 1994 [FR] France .................. 94/13724

[51] Int. Cl.[6] .................................. A61B 17/56
[52] U.S. Cl. .................. 606/61; 606/63; 606/78; 623/11; 623/16
[58] Field of Search .................. 606/78, 76, 63, 606/61, 62, 67, 68, 72, 86, 57, 58; 623/11, 12, 13, 16, 17, 18, 66, 901

[56] References Cited

U.S. PATENT DOCUMENTS

| | | | |
|---|---|---|---|
| 3,786,806 | 1/1974 | Johnson et al. | 606/78 |
| 4,157,715 | 6/1979 | Westerhoff | 606/63 |
| 4,921,499 | 5/1990 | Hoffman et al. | 623/16 |
| 5,466,261 | 11/1995 | Richelsoph | 623/16 |
| 5,516,335 | 5/1996 | Kummer et al. | 606/63 |

FOREIGN PATENT DOCUMENTS

| | | |
|---|---|---|
| 0333687 | 9/1989 | European Pat. Off. . |
| 2630161 | 10/1989 | European Pat. Off. . |
| 0 358 601 | 3/1990 | European Pat. Off. . |
| 2121922 | 1/1984 | United Kingdom . |
| 2203791 | 10/1988 | United Kingdom . |

*Primary Examiner*—Guy V. Tucker
*Attorney, Agent, or Firm*—Sughrue, Mion, Zinn, Macpeak & Seas, PLLC

[57] ABSTRACT

The present invention relates to devices for displacing two bodies relative to each other. The device of the invention is made up of two pieces respectively associated with the two bodies, a mechanism for applying a force between the two pieces, a projecting portion secured to the piece, a cavity complementary to at least a part of the projecting portion formed in the other piece, the pieces being displaceably mounted relative to each other in such a manner that the projecting portion engages in the cavity, the piece in which the cavity is formed being of a first material that is suitable for passing from an undeformable hard first state to a deformable soft second state, while the piece which is secured to the projecting portion is of a substantially undeformable second material, and a controller for controlling the passage of at least the portion of the first material that surrounds the cavity from the first state to the second state, and vice versa. The device is particularly applicable to making prostheses suitable for implanting in the human body.

14 Claims, 2 Drawing Sheets

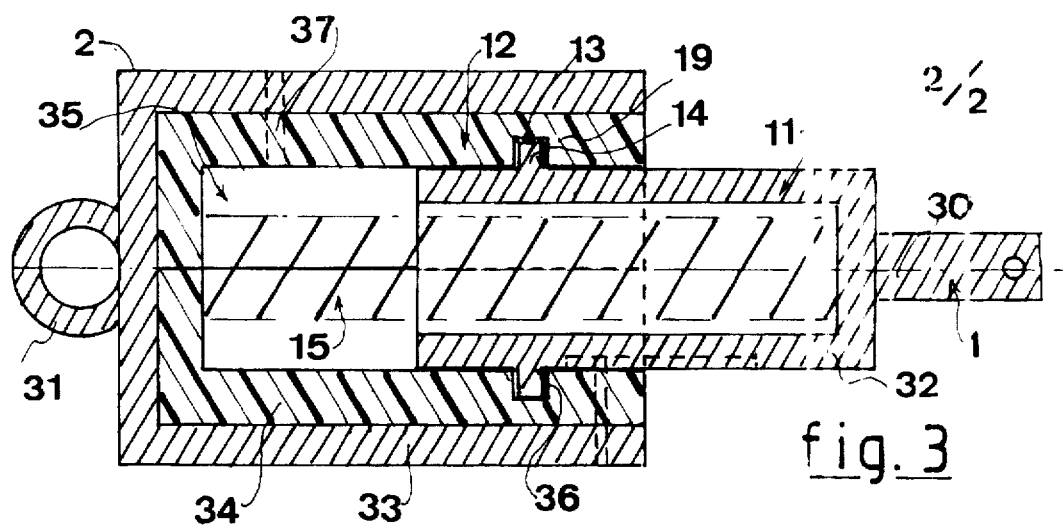
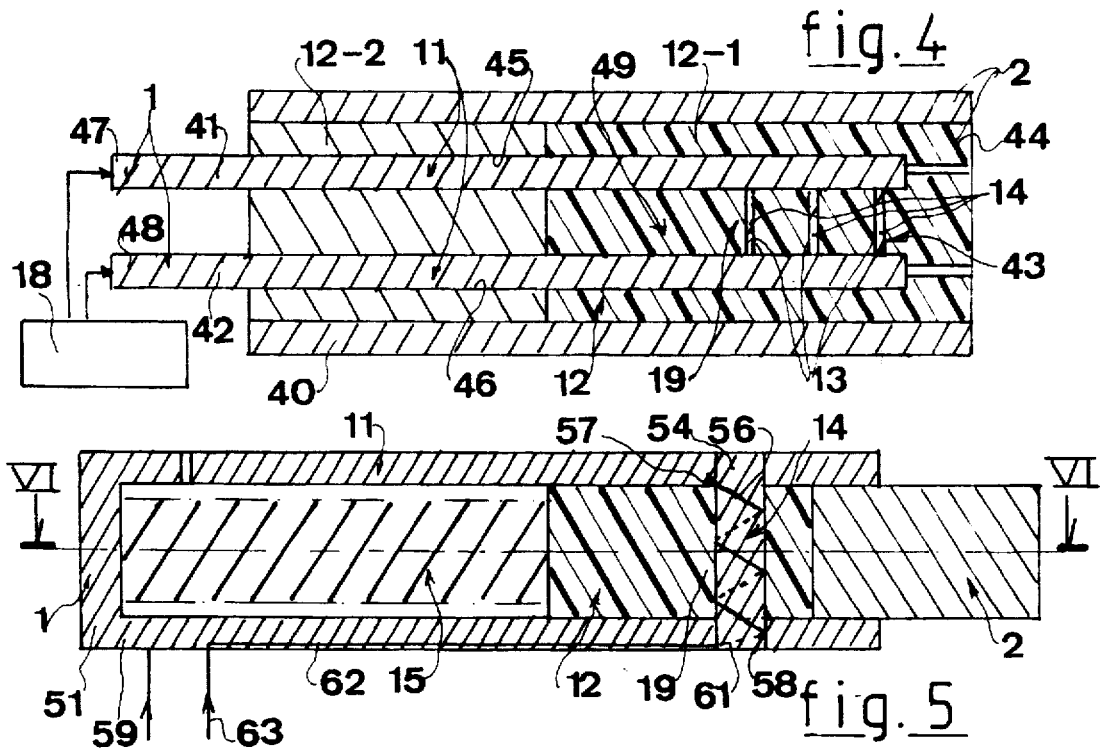
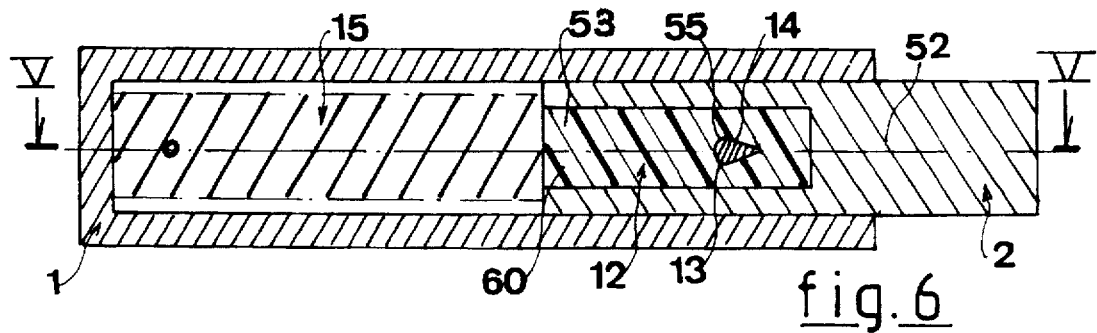

5,720,746

DEVICE FOR DISPLACING TWO BODIES RELATIVE TO EACH OTHER

The present invention relates to devices for displacing two bodies relative to each other, and having particularly advantageous applications in making prostheses suitable for being implanted in the human body, or the like.

BACKGROUND OF THE INVENTION

In numerous applications, it is necessary to displace two bodies relative to each other while simultaneously controlling such displacement. When the two bodies are uncovered or in spacious and easily accessible locations, it is relatively easy to obtain such displacement and to control it, but the same is not true when the two bodies are not directly accessible. This applies, for example, to two portions of a prosthesis implanted in a child and where it is desirable to be able to displace one portion relative to the other to reproduce growth, or to two portions of an appliance for correcting a deformation of the human body by applying stress thereto which it is desirable to renew easily by displacing the two portions of the appliance.

OBJECT AND BRIEF SUMMARY OF THE INVENTION

An object of the present invention is thus to provide a device enabling two bodies to be displaced relative to each other and having a structure that enables it to be implemented very easily even under difficult conditions of accessibility, of environment, and of size, the device thus having particularly advantageous applications in making prostheses or implantable appliances.

More precisely, the present invention provides a device for displacing first and second bodies relative to each other, wherein the device comprises:

first and second pieces;

first means for associating the first piece with the first body;

second means for associating the second piece with the second body;

means for applying a force between said two pieces;

a projecting portion secured to one of the two pieces;

a cavity formed in the other piece, said cavity being complementary in shape to at least a part of said projecting portion;

said first and second pieces being mounted for displacement relative to each other in such a manner that said projecting portion engages in said cavity;

the piece in which said cavity is made being of a first material suitable for passing from an undeformable hard first state to a deformable soft second state, and vice versa, the undeformable hard state being a state in which said projecting portion cannot deform said first material under drive from said force, and the deformable soft state being a state in which said projecting portion, under drive from said force, can penetrate into said first material in such a manner that said first material can creep around said projecting portion, while the piece carrying said projection portion is made of a second material that is substantially undeformable; and means for controlling the passage of at least the portion of the first material that surrounds the cavity from the first state to the second state, and vice versa.

BRIEF DESCRIPTION OF THE DRAWINGS

Other characteristics and advantages of the present invention appear from the following description given with reference to the accompanying illustrative but non-limiting drawings, in which:

FIG. 3 is a diagrammatic section through an embodiment of a segment of a prosthesis, e.g. intended for replacing the top portion of the tibia of a child, and making use of the device of the invention;

FIG. 4 is a diagrammatic section view showing an embodiment of a rod of variable length for surgically correcting the spine, and using a device of the invention; and FIGS. 5 and 6 are two diagrammatic longitudinal sections through an embodiment of a medullar nail used for lengthening a long bone such as the femur, by making use of a device of the invention, the section of FIG. 6 being referenced VI—VI in FIG. 5, and the section of FIG. 5 being referenced V—V in FIG. 6.

MORE DETAILED DESCRIPTION

The six above-defined figures accompanying the present description show various embodiments of a device of the invention. Nevertheless, in order to make the description easier to understand, the same references are used therein to designate elements that are the same regardless of which figure they appear in and regardless of how said elements are shown.

Figure 1:
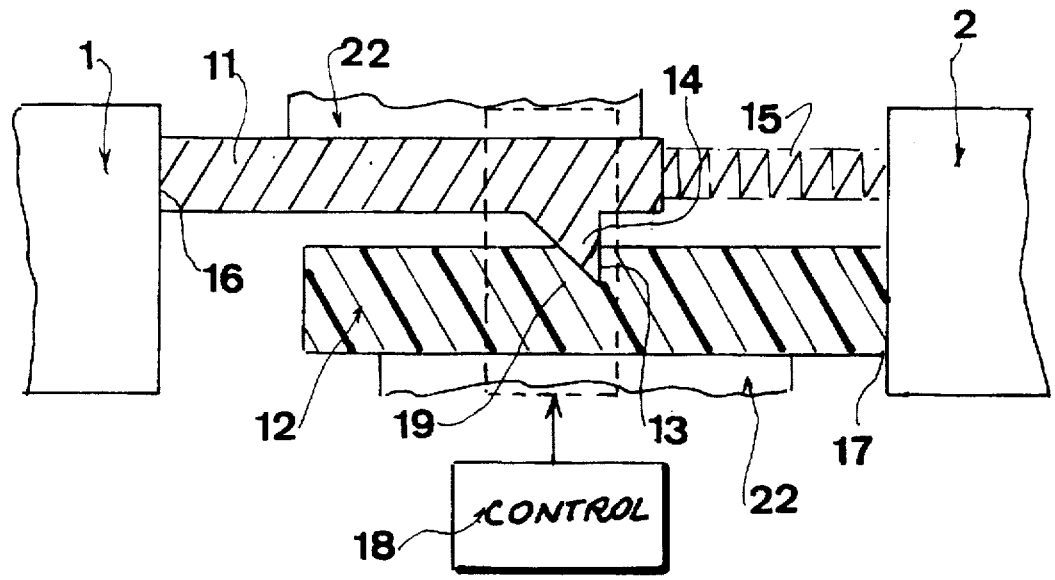
FIGS. 1 and 2 are diagrams of an embodiment of a device of the invention for displacing first and second bodies relative to each other, the figures showing two different respective states of operation.
Figure 2:
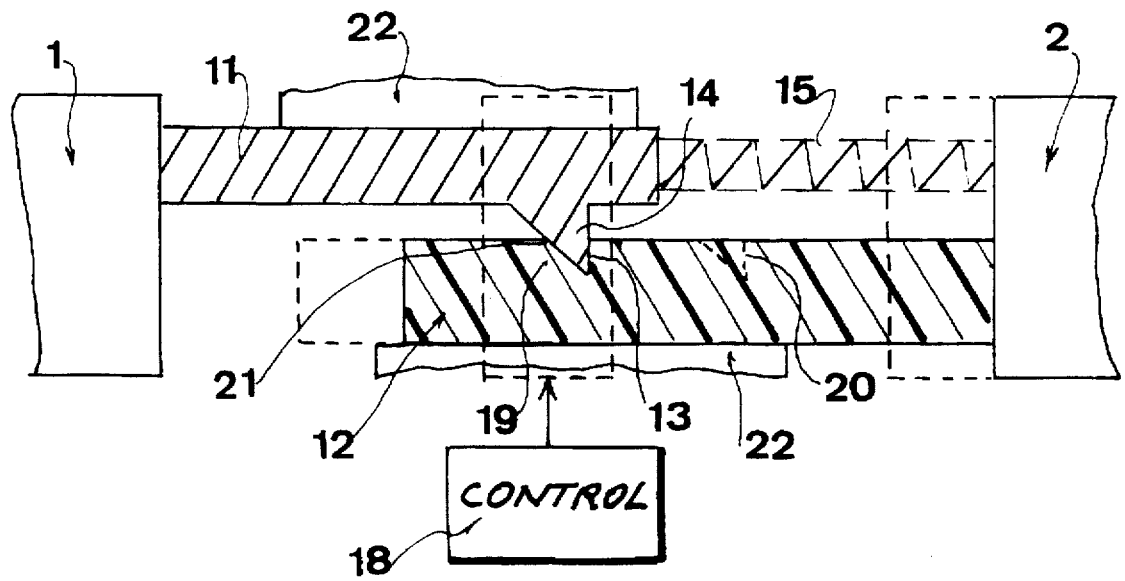

FIGS. 1 and 2 are diagrams of an embodiment of a device for displacing a first body 1 and a second body 2 relative to each other.

The device comprises a first piece 11 and a second piece 12, first means 16 for associating the first piece 11 to the first body 1, and second means 17 for associating the second piece 12 to the second body 2. Clearly, these means for associating a piece 11 or 12 to a body 1 or 2 can be of any type, and the person skilled in the art will have no difficulty in implementing such means as a function, in particular, of the natures of the materials constituting the bodies, of the natures of the materials used for making the pieces, of the functions of the elements constituting the device of the use to which the device is put, etc. Particular embodiments of the means 16 and 17 are given and/or mentioned below in the description of certain applications of the device of the invention.

Means 15 are provided for applying a force between the two pieces 11 and 12. The force may be applied directly between said two pieces, or it may be applied indirectly, e.g. via the second body 2, as shown in FIGS. 1 and 2. These means for applying a force between the two pieces 11 and 12 may likewise be of any type. They may operate in traction or in thrust, they may be resilient or the like, and they may have various different shapes. Specific embodiments of these means 15 are given below.

A projecting portion 14 secured to one of the two pieces, the piece 11 in the embodiments shown, engages in a cavity 13 made in the other piece, 12, and complementary to at least a part of the projecting portion 14. The two pieces 11 and 12 are mounted relative to each other so as to be able to be displaced as described below and so that the projecting portion 14 engages continuously in the cavity formed in the second piece 12.

To facilitate this relative displacement of the two pieces 11 and 12, and to make it safe, the device further includes means for guiding these two pieces in their displacement.

These guide means are shown diagrammatically at 22, and specific embodiments thereof are given below.

The piece 12 in which the cavity 13 is formed is made of a first material that is suitable for passing from a non-deformable hard first state to a deformable soft second state, and vice versa. Its undeformable hard state is a state in which the projecting portion 14 cannot deform the material under the drive of the force which is applied to said projecting portion, and the deformable soft state is a state in which the projecting portion 14 can move or penetrate through the material under drive from the same force, in such a manner as to enable the material to creep around said projecting portion 14. In contrast, the piece 11 to which the projecting portion 14 is secured is made of a second material that is substantially undeformable.

In the present description, the term "flow" is sometimes used instead of "creep", but naturally both terms cover the same function for obtaining the same result.

The first material can be made to pass from the first state to the second in various different ways. One of the most advantageous ways of doing this is for the first material to be suitable for softening under the action of absorbing a controlled amount of heat.

The device also includes means for controlling passage of the first material from one state to the other, and vice versa. These control means are represented diagrammatically by box 18 in FIGS. 1 and 2 which enables switching from the first state to the second state and vice versa to be controlled for at least that portion 19 of the first material defining the wall of the cavity 13 which lies ahead of the projecting portion 14 in its displacement direction under drive from the force applied to the piece 11 which is secured to said projecting portion.

The above-described device operates as follows:

It is assumed initially that the device is in the state shown in FIG. 1. The first material is in its hard, first state as defined above. Under such circumstances, the projecting portion 14 is held in abutment against the rigid wall of the cavity 13, in both the forward direction and the backward direction. The two bodies 1 and 2 are situated at a given distance from each other.

When it is desired to move the two bodies 1 and 2 apart from each other, the means 18 are used during a determined length of time to cause at least the portion 19 of the above-defined first material to change state (from the first state to the second). With the first material then being relatively soft, the projecting portion 14 is no longer retained by the hard wall of the cavity 13. Under drive from the force exerted by the means 15, which is assumed in the example shown to be a resilient thrust force, e.g. exerted by a spring, the two pieces 11 and 12 move apart from each other, entraining the two bodies 1 and 2 as they move.

During relative displacement of the piece 11 relative to the piece 12, the portion 19 of first material "creeps" or "flows" around the projecting portion 14 and fills the gap left in the piece 12 behind said projecting portion in the displacement direction of the piece 11 due to the displacement of the piece 11.

When the two pieces 11 and 12, and thus the two bodies 1 and 2 have been moved apart from each other over a determined distance, softening of the first material is stopped, e.g. by controlling the means 18. The first material returns to its undeformable hard first state, thereby presenting movement in translation of the projecting portion 14 against the front portion of the wall of the cavity 13 which, so to speak, has been "displaced" from its original position 20 shown by dashed lines in FIG. 2, to a second position 21. However, since all of the material of the piece 12 surrounding the projecting portion that penetrates therein has also returned to the hard state, the relative position of the two pieces 11 and 12 is fixed. The two pieces can no longer move either towards each other or apart from each other.

By controlling the means 18, e.g. in sequential manner, it is possible to cause at least the portion 19 of the first material constituting the piece 12 to pass from the first state to the second. It is thus possible to move the two bodies 1 and 2 progressively further apart from each other, and to do so in controlled manner.

Clearly, the same technique could be used to control moving the two bodies towards each other. Under such circumstances, the force exerted between the two pieces 11 and 12 would be a traction force and not a thrust force as in the above-described example.

The structure of the device described above is advantageous and enables the device to be used in particularly advantageous applications, specifically for making medical prostheses that can be implanted in the human body. Three such embodiments are described below.

The first embodiment shown in FIG. 3 relates to a prosthetic segment for resection of a long bone, e.g. in a child. This prosthetic segment includes all of the elements defined above with reference to FIGS. 1 and 2. In this embodiment of the device of the invention, the two bodies 1 and 2 are constituted, for example, by the ends 30 and 31 of two cylindrical tubes 32 and 33, the tube 32 constituting the piece 11 on which the above-defined projecting portion 14 is formed, the end 30 being constituted, for example, by means for connecting the prosthetic segment to the residual bone, and the end 31 being means for hinging said segment to another prostheses for constituting a joint, for example. The piece 12 is constituted by another tube 34 which has a hollow housing 35 in which the tube 32 is engaged like a cylinder-and-piston combination, thereby constituting the above-defined guide means 22 for guiding displacement of the tube 32 relative to the tube 34.

The spring 15 is situated in the hollow housing 35 and exerts a thrust force between the end of the tube 34 and the end of the tube 32.

The projecting portion 14 is in the form of a ring surrounding the outside face of the tube 32 and engaged in a complementary annular cavity 13 formed in the inside wall of the tube 34. The tube 34 is advantageously made in the form of two half-shells to facilitate assembly around the tube 32.

The tube 34 is made of a material that is tolerated well by the body, that is thermally and electrically insulating, non-magnetic, of sufficient mechanical strength particularly in compression, and capable of being softened on being heated to a temperature that is lower than the temperature to which the materials constituting the other component elements of the prosthesis can be heated, and which, on cooling after being softened by heating, recovers characteristics that are identical or at least close to its initial characteristics. By way of example, the material may be polyethylene.

The tube 32 and the projecting portion 14 may be formed integrally as a single piece of material that is thermally and electrically insulating, non-magnetic, of sufficient mechanical strength, and that is tolerated well by the body, such as zirconia ceramic, and the tube 33 may likewise be made of zirconia ceramic.

Under such circumstances, the means 18 for causing at least the portion 19 of the first material surrounding the cavity 13 to pass from the first state to the second state, and vice versa, are advantageously constituted by a conductive layer 36 deposited on the projecting portion 14 to form a closed electric loop. Such a layer can be obtained, for example, by using a plasma torch to spray a thickness of a conductive material that is tolerated well by the body, such as gold or titanium, onto the projecting portion 14 that comes into contact with the above-defined portion 19 of the first material. This closed loop is suitable for co-operating with a magnetic field source, as described below, to induce an electric current in the loop. In conventional manner, the induced electric current heats the conductive layer 36 by the Joule effect which in turn, by conduction, heats the above-defined portion of material 19, causing it to soften.

By way of example, the spring 15 is constituted by a system capable of storing and returning mechanical energy, e.g. a compression spring made of a strong material that is tolerated well by the body, such as "PHYNOX" (trademark), or indeed two contrarotating springs, or the like.

Advantageously, the hollow housing 35 is put into communication with the surrounding medium, e.g. by means of an orifice represented diagrammatically by a hole 37, to enable gas in the blood to compensate for variations in the volume of the hollow housing 35.

Also, and preferably, displacement of the tube 32 inside the tube 34 is guided linearly, e.g. by means of a pin secured to one of the two tubes having its end engaged in a groove formed in the other tube. The pin and the groove are shown in dashed lines in FIG. 3.

The person skilled in the art knows how to implant such a prosthesis, and that is not described herein.

The above-described embodiment of a prosthetic segment makes it possible to use induction from outside the body in which the prosthesis has been implanted to control geometrical changes to the segment as a function of the growth in the symmetrical healthy bone.

When it is desired to modify, in the manner described above with reference to FIG. 3, the length of the prosthetic segment which, for example, replaces the top portion of the tibia of a child, it suffices to place the length of leg containing said segment in a magnetic field that is preferably oriented perpendicularly to the closed electric loop constituted by the conductive layer 36, with the field being sufficiently intense and varying rapidly so as to induce an electric current in the thickness of the conductive material forming the closed loop, thereby generating sufficient Joule effect losses to heat by conduction and thus soften the portion 19 of the first material that is annularly adjacent to the projection portion 14, while avoiding decomposing said material by excessive heat. The tube 34 is then no longer securely retained by the projecting portion 14. The softened volume 19 flows or creeps around the projecting portion 14 from higher pressure zones to lower pressure zones, with this taking place more or less quickly depending on the viscosity of the volume of softened material 19 and on the magnitude of the forces generated by the spring 15, whose characteristics are designed to ensure that said forces are suitably greater than the opposing resistance to displacement of the projecting portion 14 through the portion 19 of the first material.

The resulting flow gives rise to the inner tube 32 being displaced relative to the tube 34 in the opposite direction to that in which the softened volume flows around the projecting portion 14. During its displacement, the inner tube 32 continues to be guided by the non-softened volume of the tube 34 and possibly by the end of the pin engaging in the corresponding groove. With the time and the intensity of heating being under control, the softened volume 19 remains at all times enclosed between non-softened portions, thereby maintaining the tubular shape of the tube 34.

Once the portion 19 of the material of the tube 34 has cooled down, the polyethylene returns to its undeformable hard consistency and the tibial segment is again capable of performing its mechanical function.

FIG. 4 shows an embodiment of an implantable appliance that makes use of the device of the invention constituted by a rod for the purpose, for example, of progressively surgically correcting the spine without requiring intermediates surgical intervention.

In the embodiment of FIG. 4, the first piece 11 is constituted by two cylindrical bars 41 and 42 mounted in parallel into complementary bores 45 and 46 formed in the second piece 12, and the projecting portion 14 is constituted in the embodiment shown by at least one rigid filament 43, and preferably a plurality of such filaments, interconnecting the two bars 41 and 42 and passing through cavities 13 formed in the portion 49 of the second piece 12 that lies between the two bars.

The above-defined guide means 22 are constituted in this embodiment by the two cylindrical bars 41 and 42 being engaged in the two complementary bores 45 and 46.

The two bars 41 & 42 and the filaments 43 are made of an electrically conductive material, but the electrical resistance per unit length of the filaments 43 is suitably greater than the electrical resistance per unit length of the bars 41 & 42.

The second piece 12 can be made as two portions 12-1 and 12-2, as shown in FIG. 4. Nevertheless, in this case, the portion 12-1 in which the cavities 13 are made may be the only portion that is made in the first material as defined above, with the other portion 12-2 being made of an electrically insulating material, e.g. a ceramic, in order to obtain good overall stiffness for the prosthetic rod.

In this example, the means 15 for exerting a force between the bars 41 & 42 and the second piece 12 are not shown specifically. In this case, these means which are required for obtaining displacement of the two bodies 1 and 2 as explained above may be constituted by any appropriate means, e.g. known external means for putting the spine of the patient in traction, or the like, acting respectively on the ends 47 & 48 of the two bars 41 & 42, and on the end 44 of the second piece 12 by means of hooks connecting the rod in conventional manner to the spine.

In order to stiffen the rod, the second piece 12 is advantageously surrounded by a sleeve 40 of hard material such as titanium.

In this embodiment, the body 1 may be constituted by the ends 47 & 48 of the two bars 41 & 42, and the body 2 may be constituted by the end 44 of the piece 12-1 and/or at least a portion of the sleeve 40.

To enable the two bars 41 & 42 to be displaced relative to the second piece 12, an electric current can be caused to pass through the two bars and the filaments 43, which current can be delivered by a source of any type as shown diagrammatically and constituting, together with the bars and the filaments, the above-defined control means 18. The current flowing along the filaments 43 is sufficiently intense to heat them and soften the portion 19 of the material of the second piece 12 adjacent to said filaments, and to enable the bars to be displaced relative to the second piece 12 in the same manner as that described above.

FIGS. 5 and 6 are two longitudinal sections through an embodiment of another implantable appliance that makes use of the device of the invention, constituting a medullar nail enabling bone to be lengthened or transported.

This appliance is designed to be inserted, for example, in the medullar channel of the bone to be treated, possibly after reaming, and it usually fills it almost completely. Each of the ends of the nail is secured by a respective external fastener to one of the bone segments that is to beloved slowly away from the other so as to stretch progressively the scar tissue that forms between the two segments after conventional osteotomy, with stretching taking place before the tissue has consolidated. The nail may be lengthened between the two points where it is fixed to segments of bone by moving its portions apart through one-fourth of a millimeter to one millimeter per day, for example.

This embodiment comprises a first piece 11 which is constituted by a hollow cylindrical tube 51 in which the second piece 12 is engaged, which second piece 12 is itself received in a reinforcing piece 52 which may constitute the second body 2.

The second piece 2 is constituted by an insert 53, e.g. made of polyethylene, in a slot 60 formed in the reinforcing piece 52. The shape of the insert is such as to ensure that it is securely held in the structure of the reinforcing piece 52 that receives it.

The spring means 15 are disposed between the end of the hollow tube 51 and the second piece 12 together with the body 2.

The projecting portion 14 is constituted by a key 54 passing through the insert 53 in a bore 55 which constitutes the above-defined cavity 13. The key is constituted, for example, by a core of mechanically strong material such as "PHYNOX" which is electrically and thermally insulated by a layer of another material that is of sufficient mechanical strength and that is insulating, such as zirconia ceramic, e.g. sprayed by means of a plasma torch.

A fine wire 56 of conductive material such as "PHYNOX" (having a diameter of 0.1 mm to 0.3 mm) is wound over the insulating layer that may optionally be machined so as to have a spiral-shaped groove to ensure that two turns of the wire do not come into contact. One end 57 of the wire is welded to the tube 51, e.g. by means of a laser, and the other end 58 is connected to a first end 61 of an electrical conductor 62 such as a gold wire insulated by a polytetrafluoroethylene sheath, for example, and running along a groove formed in the outside of the tube 51 to the closed end 59 of said tube.

It is in the wire wound on the insulating layer of the key that Joule effect losses are induced sufficient to soften the portion 19 of the first material around the key 54. The key may be streamlined so as to facilitate its displacement in the desired direction through the first material when softened.

The tube 51 and the second end 63 of the electrical conductor 62 are, for example, connected to an electric loop (not shown) which is implanted in the human body, e.g. subcutaneously. The loop can be subjected to the action of a rapidly varying magnetic field so as to induce an electric current in the loop, thereby powering the fine wire 56 which then heats up by the Joule effect as mentioned above.

The nail shown in FIGS. 5 and 6 operates in a manner that is easily deduced from the way in which the above-described prostheses operate, so it is not described more fully herein.

In the description above, several particular examples are given of the guide means 22. The means 16 and 17 for associating the pieces 11 and 12 with the bodies 1 and 2 may take up various forms. For example, in the embodiment of FIG. 3, the means 17 are constituted by the tube 34 being engaged in the tube 33, with the tube 34 also being secured to the tube 33 by any other means such as adhesive, keying, a nut, or the like. In that embodiment, the means 16 are constituted by at least a portion of the piece 11 itself or an auxiliary piece secured to the piece 11 by any appropriate means such as welding, being formed integrally therewith, etc. The means 16 and 17 are not described in detail for the embodiments shown in FIG. 4 or in FIGS. 5 and 6, but the person skilled in the art will be able to implement them without any difficulty.

In the above-described examples, the displacement of the two bodies relative to each other is constituted by linear translation. Nevertheless, it is clear that the invention can be applied to any other kind of movement such as rotation, twisting, or any combination of such kinds of movement together with translation.

I claim:

1. A device for displacing first and second bodies relative to each other, wherein the device comprises:

first and second body;

first means for associating the first piece with the first body;

second means for associating the second piece with the second body;

means for applying a force between said two pieces;

a projecting portion secured to one of the two pieces;

a cavity formed in the other piece, said cavity being complementary in shape to at least a part of said projecting portion;

said first and second pieces being mounted for displacement relative to each other in such a manner that said projecting portion engages in said cavity;

the piece in which said cavity is made being of a first material suitable for passing from an undeformable hard first state to a deformable soft second state, and vice versa, the undeformable hard state being a state in which said projecting portion cannot deform said first material under drive from said force, and the deformable soft state being a state in which said projecting portion, under drive from said force, can penetrate into said first material in such a manner that said first material can creep around said projecting portion, while the piece carrying said projection portion is made of a second material that is substantially undeformable; and means for controlling the passage of at least the portion of the first material that surrounds the cavity from the first state to the second state, and vice versa.

2. A device according to claim 1, further including means for guiding said first and second pieces in their displacement.

3. A device according to claim 1, wherein the means for controlling the passage of at least the portion of the first material that surrounds the cavity from the first state to the second state, and vice versa, are means for softening at least the portion of the first material which defines the wall of said cavity lying in front of said projecting portion in the displacement direction of the piece to which said projecting portion is secured, said softening being obtained by the action of controlled heat absorption.

4. A device according to claim 1, wherein said first piece is constituted by a first tube and said second piece is constituted by a second tube having a hollow first housing, said first tube being engaged in said hollow first housing.

5. A device according to claim 4, wherein said means for applying a force between said two pieces are constituted by a spring situated in said hollow first housing between the respective ends of the first and second tubes.

6. A device according to claim 4, wherein the projecting portion is in the form of a ring surrounding said first tube on the outside face thereof and engaging in said cavity which is in the form of an annulus formed in the inside wall of said second tube.

7. A device according to claim 6, wherein said means for controlling the passage of at least the portion of the first material that surrounds the cavity from the first state to the second state, and vice versa, include a conductive layer deposited on said annular projecting portion to form a closed electric loop suitable for cooperating with a magnetic field source.

8. A device according to claim 4, wherein first piece is constituted by a third hollow cylindrical tube, said second piece being engaged in said third tube.

9. A device according to claim 8, wherein said second piece is constituted by an insert situated in a slot formed in a reinforcing piece.

10. A device according to claim 9, wherein said projecting portion is constituted by at least one key passing right through said insert.

11. A device according to claim 10, wherein said key is constituted by a core of mechanically strong material that is electrically and thermally insulated by a layer of mechanically strong material that is insulating.

12. A device according to claim 11, wherein the means for controlling the passage of at least the portion of the first material that surrounds the cavity from the first state to the second state, and vice versa, comprise at least one fine wire of conductive material wound on said key, an electric current source, and means for coupling said source to said fine wire.

13. A device according to claim 1, wherein said first piece is constituted by two cylindrical bars mounted in parallel in two complementary bores formed in said second piece, the projecting portion being constituted by at least one rigid filament interconnecting said two bars.

14. A device according to claim 13, wherein the means for controlling the passage of at least the portion of the first material that surrounds the cavity from the first state to the second state, and vice versa comprise at least one electric current source connected to the two bars, said bars and said rigid filament being of an electrically conductive material, the electrical resistance per unit length of said filament being greater than the electrical resistance per unit length of said bars, said first material from which said second piece is made being a material that is not electrically conductive.

* * * * *